United States Patent
Abhishek et al.

(10) Patent No.: US 9,529,335 B2
(45) Date of Patent: Dec. 27, 2016

(54) TIMER BASED ON CHEMICAL SENSING

(71) Applicant: Palo Alto Research Center Incorporated, Palo Alto, CA (US)

(72) Inventors: Ramkumar Abhishek, Mountain View, CA (US); Sourobh Raychaudhuri, Mountain View, CA (US); Ashish Pattekar, Cupertino, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 131 days.

(21) Appl. No.: 14/473,302

(22) Filed: Aug. 29, 2014

(65) Prior Publication Data

US 2016/0062318 A1  Mar. 3, 2016

(51) Int. Cl.
| | |
|---|---|
| G04F 1/00 | (2006.01) |
| G04F 7/00 | (2006.01) |
| G01N 31/22 | (2006.01) |
| A61J 7/04 | (2006.01) |
| B65D 75/36 | (2006.01) |
| B65D 75/54 | (2006.01) |
| A61M 5/31 | (2006.01) |

(52) U.S. Cl.
CPC ............... *G04F 7/00* (2013.01); *A61J 7/0409* (2013.01); *B65D 75/367* (2013.01); *B65D 75/54* (2013.01); *G01N 31/229* (2013.01); *G04F 1/00* (2013.01); *A61J 7/0427* (2015.05); *A61J 2200/70* (2013.01); *A61M 5/31* (2013.01)

(58) Field of Classification Search
CPC ................ G04F 1/00; G01N 31/222
USPC .......................................... 368/327
See application file for complete search history.

(56) References Cited

U.S. PATENT DOCUMENTS

| | | | | |
|---|---|---|---|---|
| 4,098,120 A * | 7/1978 | Manske | ............... | G01N 31/222 116/200 |
| 5,112,768 A * | 5/1992 | Carver | ................ | G01N 31/222 116/206 |
| 5,293,996 A * | 3/1994 | Duncan | ................ | B65D 81/268 206/204 |
| 5,318,181 A * | 6/1994 | Stover | ............... | H05K 13/0084 206/204 |
| 5,875,892 A * | 3/1999 | Martin | .............. | H01L 21/67253 116/206 |
| 6,529,446 B1 * | 3/2003 | de la Huerga | ........ | A61J 7/0084 368/10 |
| 6,536,370 B2 * | 3/2003 | Paton | ................... | G01N 31/222 116/206 |
| 6,698,378 B1 * | 3/2004 | Dick | .................... | G01N 31/222 116/206 |

(Continued)

*Primary Examiner* — Amy Cohen Johnson
*Assistant Examiner* — Jason Collins
(74) *Attorney, Agent, or Firm* — Hollingsworth Davis, LLC

(57) ABSTRACT

An elapsed timer device includes a timer element comprising a timer chamber, a timer chamber conditioning material disposed within the timer chamber, and a sensor arranged to sense a timer chemical within the timer chamber. The sensor indicates elapsed time in response to a threshold level of the chemical being present within the timer chamber. The timer chamber, timer chemical adsorption/desorption characteristics of the timer chamber conditioning material, and the sensor are configured so that an amount of the timer chemical within the timer chamber reaches the threshold level within a predetermined time after initialization of the timer element.

29 Claims, 16 Drawing Sheets

(56) References Cited

U.S. PATENT DOCUMENTS

| | | | |
|---|---|---|---|
| 7,294,379 B2* | 11/2007 | Ko | G01K 3/04 |
| | | | 368/327 |
| 7,456,744 B2 | 11/2008 | Kuhns et al. | |
| 7,769,494 B1 | 8/2010 | Simon et al. | |
| 8,619,507 B2* | 12/2013 | Ambrozy | G01K 3/04 |
| | | | 116/200 |
| 2008/0143191 A1 | 6/2008 | Laser | |
| 2008/0245289 A1* | 10/2008 | Shiraishi | B32B 5/00 |
| | | | 116/206 |
| 2013/0242707 A1* | 9/2013 | Kodat | G04C 23/04 |
| | | | 368/10 |

* cited by examiner

TIMER BASED ON CHEMICAL SENSING

TECHNICAL FIELD

This application relates generally to timer devices. The application also relates to components, systems, and methods pertaining to such devices.

BACKGROUND

Timer devices including elapsed time indicators can be particularly useful to monitor pharmaceuticals, food products, and other items that have an expiration date. In many applications, it is desirable to use passive elapsed time indicators that do not require connection to a battery or other power source.

SUMMARY

Various embodiments described herein involve an elapsed timer device. According to some embodiments, an elapsed timer device includes at least one timer element comprising a timer chamber, a timer chamber conditioning material disposed within the timer chamber, and a sensor arranged to sense a timer chemical within the timer chamber. The sensor indicates elapsed time in response to a threshold level of the timer chemical being present within the timer chamber. The timer chamber, the timer chemical adsorption/desorption characteristics of the timer chamber conditioning material, and the sensor are configured so that an amount of the timer chemical within the timer chamber reaches the threshold level within a predetermined time after initialization of the timer element.

According to some aspects, the at least one timer element includes multiple timer elements. Each of the timer elements are configured to time different elapsed times. The sensors of the timer elements are configured so that they sequentially indicate the different elapsed time.

According to some aspects, the device includes a first layer having the timer chamber conditioning material arranged on or embedded at least partially within the first layer, a second layer that includes the sensor, and spacers arranged between the first layer and the second layer, wherein the timer chamber is disposed between the first and second layers. The device may include a third layer, wherein an initialization chamber is formed between the third and first layers. The third layer has a timer chamber conditioning material arranged on or embedded at least partially within the third layer.

According to various aspects, the elapsed timer device may be flexible. For example, the elapsed timer device may be made of a flexible polymer. According to some implementations, the elapsed timer device forms at least a portion of a label. In some implementations, the elapsed timer device may be arranged to measure elapsed time from the use of a product dispenser, e.g., a most recent use. For example, the product dispenser, such as an insulin pen or pill bottle, can be configured to dispense a pharmaceutical, drug, or other product. The product dispenser may be a blister pack comprising a plurality of cells containing a product to be dispensed, wherein the elapsed timer is configured to measure an elapsed time from a dispensing of the product from any of the plurality of cells.

Some embodiments involve an elapsed timer device comprising at least one timer element that includes a timer chamber, a humidity conditioning material disposed within the timer chamber, and a humidity sensor arranged to sense humidity within the timer chamber and to indicate elapsed time in response to a threshold humidity level being present within the timer chamber. The timer chamber, adsorption/desorption characteristic of humidity conditioning material, and the humidity sensor are configured so that an amount of humidity within the timer chamber reaches the threshold humidity level within a predetermined time after initialization of the timer element.

According to some aspects, the timer chamber includes a timer chamber initialization structure, wherein the initialization of the timer element comprises operation of the initialization structure. For example, initialization structure may comprise at least one of a hole, a porous material, a gas exchange membrane, and a valve.

The elapsed timer device may include an initialization chamber, wherein the timer chamber initialization structure is arranged so that when the timer chamber initialization structure is open, the timer chamber is fluidically coupled to the initialization chamber. In some implementations, a humidity conditioning material is disposed within the initialization chamber. At steady-state, the humidity conditioning material within the initialization chamber maintains a predetermined humidity within the initialization chamber.

The initialization chamber may include an initialization chamber initialization structure arranged so that when the initialization chamber initialization structure is open, the initialization chamber is fluidically coupled to an environment external to the elapsed timer device.

The at least one elapsed timer device may include multiple timer elements. When open, initialization structures of the timer chambers fluidically connect the timer chambers to the initialization chamber. According to some implementations, each timer chamber includes a vent configured to facilitate air exchange.

According to some aspects, the elapsed timer device includes multiple timer elements wherein each timer element is each configured to time a different elapsed time. The humidity sensors of the timer elements sequentially indicate the elapsed times timed by the timer elements. For example, each of the humidity sensors may comprise a moisture-sensitive chemical that changes color at a predetermined humidity.

Some embodiments are directed to a method that includes initializing at least one timer element. Moisture in the timer chamber of the timer element is adsorbed or desorbed using a humidity conditioning material. Humidity in the timer chamber is sensed using a humidity sensor. The elapsed time is indicated in response a threshold humidity level being present within the timer chamber. The timer chamber, adsorption/desorption characteristic of the humidity conditioning material, and the humidity sensor are configured so that the amount of humidity within the timer chamber reaches the threshold humidity level within a predetermined time after initialization of the timer element.

Initializing the at least one timer element comprises activating a timer chamber initialization structure, the activation of the timer chamber initialization structure allowing air having a predetermined humidity from an initialization chamber into the timer chamber.

Initializing the at least one timer element may involve initializing a plurality of timer elements. Each of the timer elements may be configured to indicate a different elapsed time. For example, in some embodiments the elapsed time may be visually indicated.

According to some aspects, the method involves dispensing a product, the dispensing of the product triggering the initializing of the at least one timer element.

Some embodiments involve a method for timing elapsed time. The method includes initializing at least one timer element, the initializing starting a chemical reaction in the timer chamber of the timer element that produces a timer chemical. The timer chemical is adsorbed or desorbed in the timer chamber by a timer chamber conditioning material. The timer chemical in the timer chamber is sensed using a sensor. The elapsed time is indicated in response to a threshold level of the timer chemical being present within the timer chamber. The timer chamber, timer chemical adsorption/desorption characteristic of the timer chamber conditioning material, and the sensor are configured so that an amount of the timer chemical within the timer chamber reaches the threshold level within a predetermined time after initialization of the timer element.

BRIEF DESCRIPTION OF THE DRAWINGS

The figures are not necessarily to scale. Like numbers used in the figures refer to like components. However, it will be understood that the use of a number to refer to a component in a given figure is not intended to limit the component in another figure labeled with the same number.

DESCRIPTION

Figure 1:
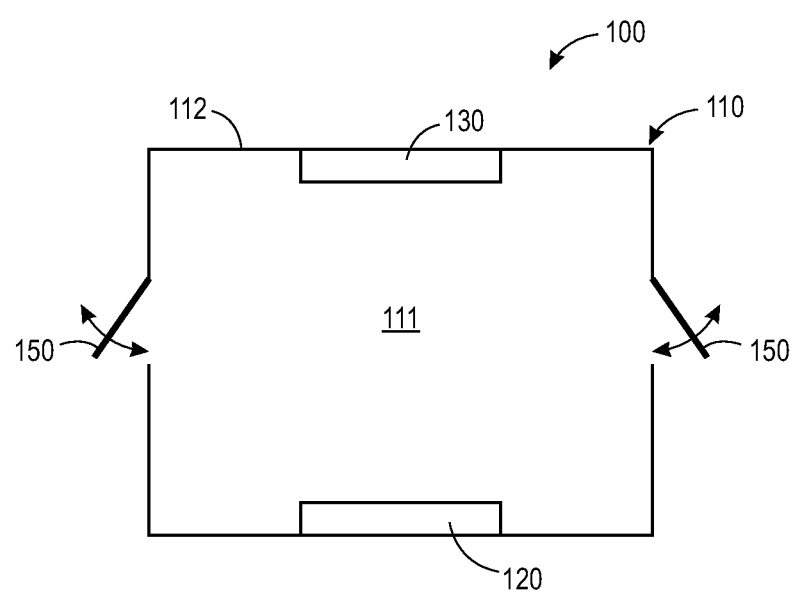
FIG. 1 illustrates an elapsed timer device in accordance with some embodiments.

Embodiments described herein involve timing devices that indicate elapsed time based on chemical sensing. FIG. 1 illustrates an elapsed timer device 100 in accordance with some embodiments. The device 100 includes at least one timer element 110 that includes a timer chamber 111 enclosed by one or more chamber walls 112. The device 100 illustrates a single timer element 110 having a predetermined volume, although multiple timer elements could be used as described in more detail below. The timer element 110 includes a timer chamber conditioning material (TCCM) 120 disposed within the timer chamber 111. The TCCM has a predetermined adsorption/desorption characteristic with respect to a timer chemical.

An initialization structure 150 is arranged to initialize the timer element, wherein the initialization leads to an amount of a timer chemical being increased or decreased in the timer chamber. The TCCM operates to adsorb or desorb the timer chemical toward a threshold level.

The timer element 110 further includes a sensor 130 arranged to sense the timer chemical within the timer chamber 111 and to indicate elapsed time in response to a threshold level of the timer chemical being present within the timer chamber 111. Geometry (e.g., volume and/or shape) of the timer chamber 111, the adsorption/desorption characteristics of the TCCM 120, and the chemical sensing characteristics of the sensor 130 are calibrated so that the amount of the timer chemical within the timer chamber 111 reaches the threshold level of the sensor within a predetermined time after initialization of the timer element 110.

In some embodiments, initialization involves releasing the timer chemical into the timer chamber, thereby increasing an amount of the timer chemical in the timer chamber. In various embodiments, initialization of the timer element involves initializing the timer chamber, e.g., by releasing a first reactant into the timer chamber that reacts with a second reactant to increase or decrease an amount of the timer chemical in the timer chamber. In some embodiments, initialization involves releasing air (or other initialization substance) into the timer chamber, wherein the release of initialization substance reacts with a first reactant or starts a chemical reaction between a first reactant and a second reactant in the timer chamber to increase or decrease the amount of the timer chemical.

The TCCM is configured to adsorb and/or desorb the timer chemical to maintain a predetermined amount of the timer chemical in the timer chamber. In some embodiments the timer chemical changes from one state to another state during and/or after the adsorption or desorption of the timer chemical by the TCCM. For example, the timer chemical may change from liquid to gas. In other embodiments the timer chemical does not undergo a state change.

The threshold level of the sensor may be reached when the TCCM absorbs the timer chemical to decrease an amount of the timer chemical in the timer chamber below the threshold level. In some embodiments, the threshold level of the timer chemical may be reached when the TCCM desorbs the timer chemical to increase an amount of the timer chemical in the timer chamber above the threshold level.

In some embodiments, the elapsed timer device is based on humidity, e.g., the timer chemical is water vapor in the timer chamber. The timer element 110 includes a humidity conditioning material as the TCCM 120 having predetermined moisture adsorptive/desorptive characteristics which is disposed within a timer chamber 111 having a predetermined volume. An initialization structure 150 is arranged to initialize the timer element, wherein the initialization begins the elapsed time measurement. The timer element 110 further includes a sensor 130 arranged to sense humidity within the timer chamber 111 and to indicate elapsed time in response to a threshold humidity level being present within the timer chamber 111. Geometry (e.g., volume and/or shape) of the timer chamber 111, the adsorption/desorption characteristics of the TCCM 120, and the humidity sensing characteristics of the sensor 130 are calibrated so that the humidity within the timer chamber 111 reaches the threshold humidity level of the humidity sensor within a predetermined time after initialization of the timer element 110.

In some embodiments, the elapsed timer device is based on camphor, e.g., the timer chemical is camphor vapor in the timer chamber. The timer element 110 includes camphor conditioning material as the TCCM 120 having predetermined sublimating characteristic which is disposed within a timer chamber 111 having a predetermined volume. An initialization structure 150 is arranged to initialize the timer element, wherein the initialization begins the elapsed time measurement. The timer element 110 further includes a sensor 130 arranged to sense camphor vapor within the timer chamber 111 and to indicate elapsed time in response to a threshold camphor vapor level being present within the timer chamber 111. Geometry (e.g., volume and/or shape) of the timer chamber 111, the sublimating characteristics of the camphor conditioning material 120, and the camphor vapor sensing characteristics of the sensor 130 are calibrated so that the amount of camphor vapor within the timer chamber 111 reaches the threshold camphor vapor level of the camphor vapor sensor within a predetermined time after initialization of the timer element 110.

In some embodiments, the elapsed timer device is based on carbon dioxide, e.g., the timer chemical is carbon dioxide vapor in the timer chamber. The timer element 110 includes carbon dioxide conditioning material as TCCM 120 (e.g., dry ice) having predetermined adsorptive/desorptive/sublimating characteristic which is disposed within a timer chamber 111 having a predetermined volume. An initialization structure 150 is arranged to initialize the timer element, wherein the initialization begins the elapsed time measurement. The timer element 110 further includes a sensor 130 arranged to sense carbon dioxide vapor within the timer chamber 111 and to indicate elapsed time in response to a threshold carbon dioxide vapor level being present within the timer chamber 111. Geometry (e.g., volume and/or shape) of the timer chamber 111, the adsorptive/desorptive/sublimating characteristics of the carbon dioxide conditioning material 120, and the carbon dioxide vapor sensing characteristics of the carbon dioxide vapor sensor 130 are calibrated so that the amount of carbon dioxide vapor within the timer chamber 111 reaches the threshold carbon dioxide vapor level of the carbon dioxide vapor sensor within a predetermined time after initialization of the timer element 110.

Examples discussed below rely on humidity sensing for describing timer structures and methods. It will be appreciated that the concepts described using these examples can also be applied in general to a chemical elapsed timer device as discussed in connection with FIG. 1.

FIGS. 2A through 2E illustrate operation of an elapsed timer device 200 in accordance with various embodiments. The timer element 210 of the elapsed timer device 200 is initialized at time $t_1$ and indicates the passage of an amount of elapsed time $\Delta t_e$, at time $t_3$. In this example, the humidity sensor 230 comprises a relative humidity (RH) sensor and indicator. The humidity sensor/indicator 230 changes color when the humidity in the timer chamber 211 reaches a threshold humidity. The timer chamber 211, humidity conditioning material (HCM) 220, and humidity sensor/indicator 230 are calibrated so that a predetermined period of time passes, $\Delta t_e$, from initialization of the timer element 210 until a change in the color of the humidity sensor/indicator 230. In this example, the timer chamber 211 has a rectangular cross section, although a timer chamber with another cross sectional shape, e.g., round, square, hexagonal cross section could alternatively be used.

Figure 2A:
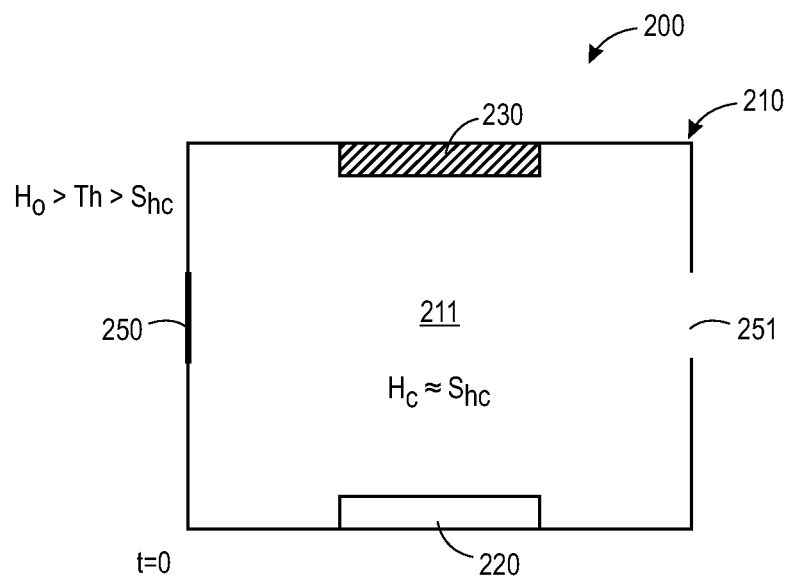
FIGS. 2A through 2E illustrate operation of an elapsed timer device.

FIG. 2A shows an elapsed timer device 200 comprising a timer element 210 at time t=0. At time t=0, the timer chamber 211 has not yet been initialized and the timer element 210 is at steady state. The relative humidity (RH) inside the timer chamber 211 is controlled by the adsorptive/desorptive characteristics of the humidity conditioning material (HCM) 220 disposed within the timer chamber 211. Suitable humidity conditioning materials include silica gel and/or humidity conditioning products such as Art Sorb, available from Creative Humidity, located in Raleigh, N.C., and manufactured by Fuji Silysia Chemical Ltd. (http://www.fuji-silysia.co.jp/english/index.html). The adsorptive/desorptive characteristics of the humidity conditioning material can be designed to adsorb or desorb moisture within the timer chamber such that, for a given initialization RH, the HCM brings the RH within timer chamber 211 to the threshold value of the humidity sensor within a predetermined amount of time. The RH setpoint value of the HCM 220 in the example of FIG. 2 is $S_{hc}$. In this example, the HCM 220 is configured to adsorb moisture until the RH in the vicinity of the humidity conditioning material is about equal to the setpoint, $S_{hc}$. At t=0, the timer chamber 211 is at steady state, the relative humidity, $H_c$, within the timer chamber 211 is approximately equal to the setpoint of the HCM, $S_{hc}$. The relative humidity, $H_o$, outside the timer chamber 111 is greater than $S_{hc}$.

In some implementations, the humidity sensor 230 is a humidity indicating card (HIC), although other types of humidity sensors and indicators may be used to sense and indicate humidity. The HIC 230 is sensitive to the RH in the timer chamber 211 and, in this example, indicates when the humidity falls below the threshold value of the HIC 230, denoted Th in FIGS. 2A through 2E. For example, the HIC 230 may be a moisture-sensitive chemical that will change color when the RH in the timer chamber 211 falls below Th. Such an HIC may be made of blotting paper impregnated with cobalt (II) chloride or copper (II) chloride base. In the example of FIGS. 2A through 2E, $H_o > Th > S_{hc}$. At t=0, the color of the HIC 230 (shaded in FIG. 2A) indicates that the RH in the timer chamber is below Th. The color change of the HIC may be reversible which allows the timing device to be reusable.

Figure 2B:
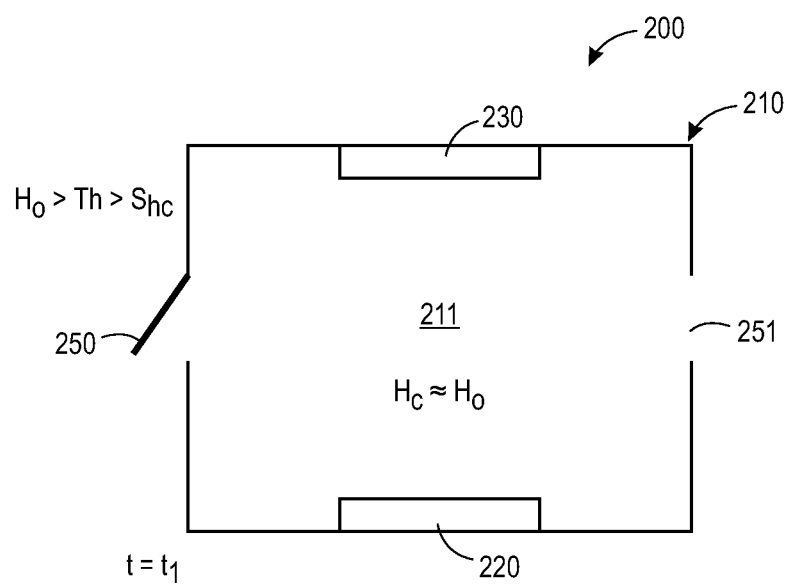

FIG. 2B shows the timer element 210 at time $t=t_1$, shortly after the timer element 210 is initialized. Initialization involves operating the initialization structure 250, such as by opening a valve puncturing a covering, or other operation. The initialization changes the RH inside the timer chamber 211, e.g., by allowing air from outside the chamber 211 to enter the interior of the timer chamber 211. In some embodiments, the initialization structure 250 may comprise a small hole or a porous membrane that allows air to pass into the timer chamber 211. In some embodiments, the initialization structure 250 is operated by a piston (not shown in FIG. 2A) such that when the piston is depressed, air is forced into the timer chamber through the initialization structure 250. The timer chamber 211 may additionally include a vent 251 to facilitate air displacement during initialization.

Just after initialization, at time $t_1$, the RH inside the chamber 211 is approximately equal to the RH of the outside air, $H_c \approx H_o$ and the RH inside the chamber 211 exceeds the setpoint, $S_{hc}$, of the HCM 220 and also exceeds the threshold, Th, of the HIC 230. The color of the humidity sensor/indicator 230 (unshaded in FIG. 2B) indicates that the RH within the timer chamber 211 is greater than the Th of the humidity sensor/indicator 230.

Figure 2C:
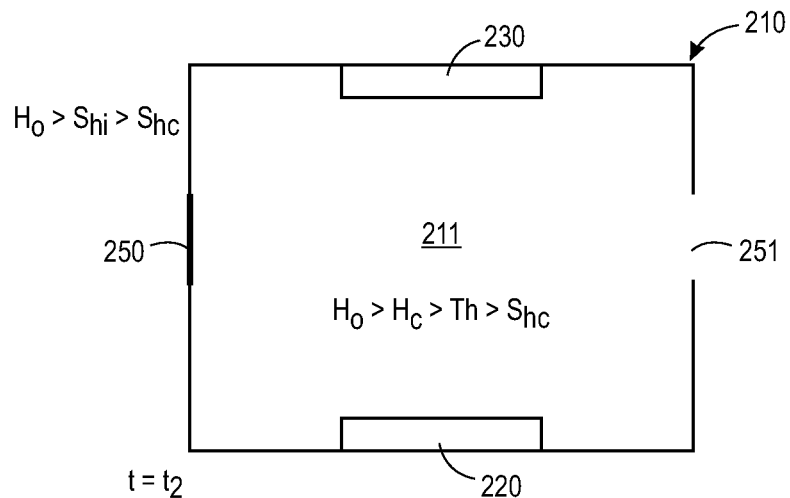

After initialization, the initialization structure 250 may be closed or arranged to substantially block further introduction of air from outside the timer chamber. The HCM 220 adsorbs moisture from the air in the timer chamber 211, which decreases the RH in the timer chamber 211. FIG. 2C illustrates the timer element 210 at time t=t2, at which time the humidity, $H_c$, in the timer chamber 211 is greater than both the threshold of the humidity sensor 230 and the setpoint of the HCM 220. Because $H_c > Th$, the color of the humidity sensor/indicator 230 remains unshaded in FIG. 2C.

Figure 2D:
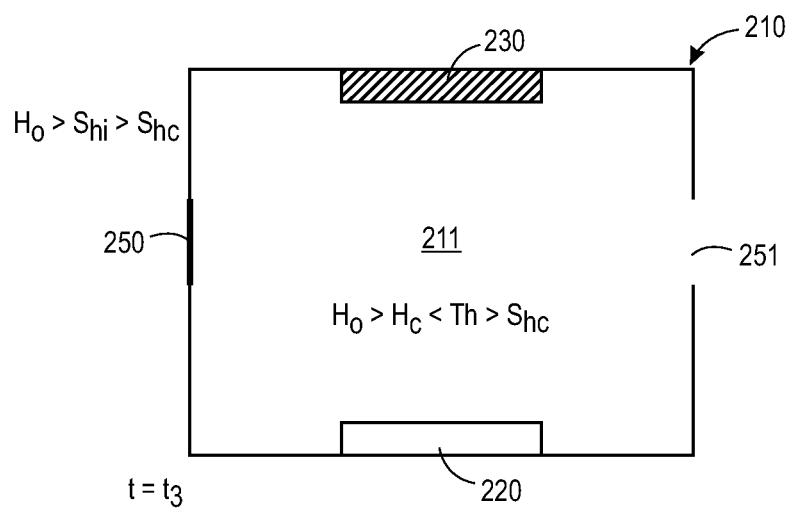
Figure 2E:
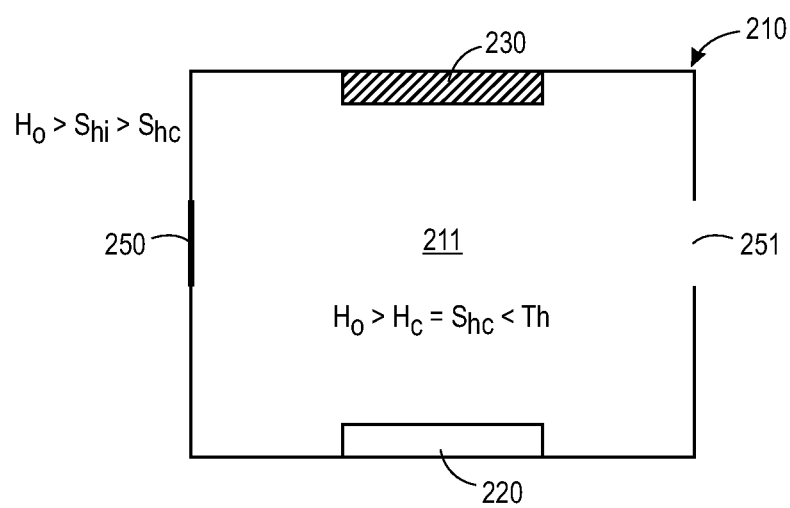

As shown in FIG. 2D, the HCM 220 continues to adsorb moisture, and the RH in the timer chamber 211 continues to drop until $H_c$ is below the threshold of the humidity sensor 230. At time $t=t_3$, the RH is below the threshold of the humidity sensor/indicator 230, causing the humidity sensor/indicator 230 to change color (shaded in FIG. 2D). The HCM 220 continues to adsorb moisture in the timer chamber 211 until the RH in the timer chamber is about equal the setpoint of the HCM 220 (FIG. 2E). In some embodiments, the timer device may be a multi-use device that can be re-initialized to re-start the elapsed timer. In some embodiments, the timer device may be a single use, disposable elapsed timer.

Figure 3:
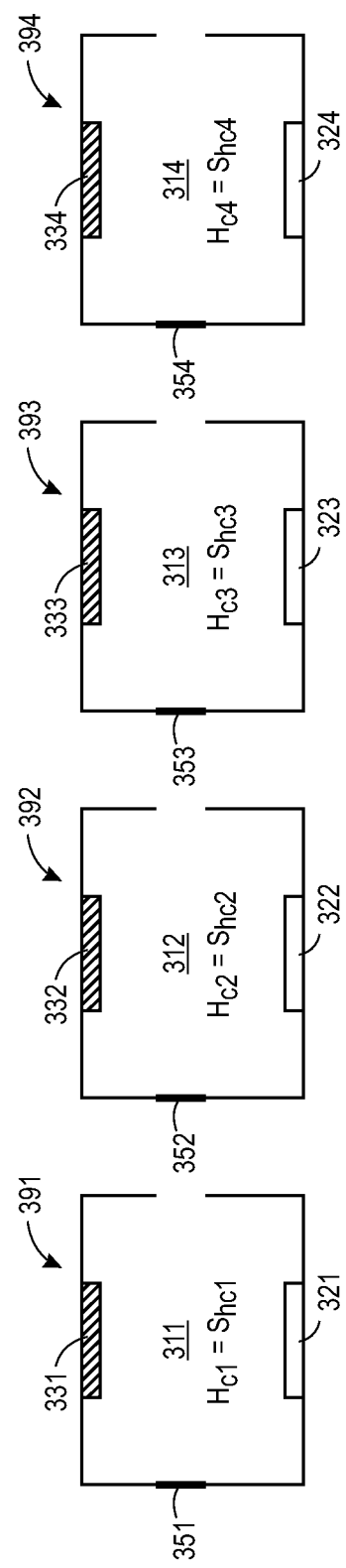
FIG. 3 depicts an elapsed timer device having multiple timer chambers.

FIGS. 2A through 2E illustrate operation of an elapsed timer device comprising a single timer element. In some embodiments, the elapsed timer device may comprise multiple timer elements, each timer element configured to measure and indicate a different amount of elapsed time. FIG. 3 depicts a multiple timer element elapsed timer device 300 comprising timer elements 391-394. Each of the timer elements 391-394 is initialized at time $t=t_1$, e.g., by substantially simultaneously operating initialization structures 351-354. Each of the timer elements 391-394 may be designed to indicate a different amount of elapsed time from the other timer elements.

As indicated in FIG. 3, timer element 391 includes a timer chamber 311, HCM 321 disposed within the timer chamber 311, and humidity sensor/indicator 331; timer element 392 includes a timer chamber 312, HCM 322 disposed within the timer chamber 312, and humidity sensor/indicator 332; timer element 393 includes a timer chamber 313, HCM 323 disposed within the timer chamber 313, and humidity sensor/indicator 333; and timer element 394 includes a timer chamber 314, HCM 324 disposed within the timer chamber 314, and humidity sensor/indicator 334. The timer chamber 311, HCM 321, and humidity sensor 331 of the first timer element 391 is designed to indicate passage of elapsed time, $\Delta t_{e1}$. The timer chamber 312, HCM 322, and humidity sensor 332 of the second timer element 392 is designed to indicate passage of elapsed time, $\Delta t_{e2} > \Delta t_{e1}$. The timer chamber 313, HCM 323, and humidity sensor 333 of the second timer element 393 is designed to indicate passage of elapsed time, $\Delta t_{e3} > \Delta t_{e2}$. The timer chamber 314, HCM 324, and humidity sensor 334 of the second timer element 394 is designed to indicate passage of elapsed time, $\Delta t_{e4} > \Delta t_{e3}$. In this configuration, after initialization, the humidity sensors/indicators 331, 332, 333, 334 will change color sequentially to indicate the elapsed times $\Delta t_{e1}$, $\Delta t_{e2}$, $\Delta t_{e3}$, $\Delta t_{e4}$.

Figure 4:
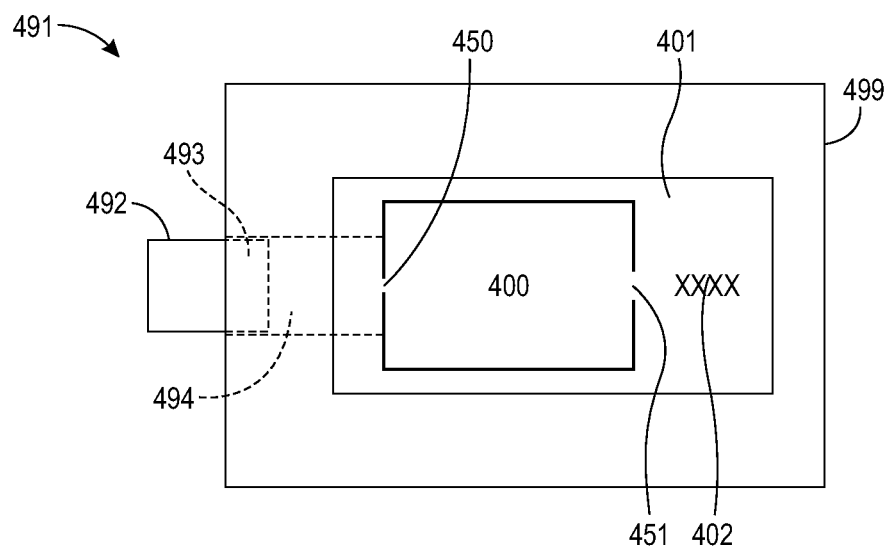
FIG. 4 illustrates an elapsed timer device that is part of a label disposed on a container in accordance with some embodiments.

In some embodiments, the elapsed timer device disclosed herein can be fabricated from flexible materials, making the timer device particularly useful as a label or other flexible indicator that can be adhered or otherwise attached to a container or other packaging. FIG. 4 illustrates an elapsed timer device 400 that is part of a label 401 disposed on a container 499. The label 401 may also include markings 402, e.g., text or graphics, identifying the product contained within. The container 499 can include an actuator 491 that operates the initialization structure 450 of the elapsed timer device 400. As shown in FIG. 4, the actuator 491 may include a button 492 that can be operated by a user. The button 492 is coupled to move a piston 493 in a cylinder 494. In this example, when the button 492 is depressed, the piston 493 moves in the cylinder 493 and air is forced from the outside environment through the initialization structure (hole 450) into the timer chamber(s) of the timer device 400 to initialize the timer element(s). Vent 451 facilitates air displacement within the timer chamber of the timer device 400. After the actuator 491 operates the initialization structure to initialize the timer chamber(s), the timer device 400 indicates the elapsed time since the initialization.

In some embodiments, an initialization chamber may be used to control the RH of the air introduced at initialization into the one or more timer chambers of an elapsed timer device. FIGS. 5A through 5G illustrate operation of an elapsed timer device 500 that includes an initialization chamber. In this example, the elapsed timer device 500 is implemented as a portion of a label 501 for an insulin pen 599. In this example, the elapsed timer device 500 is configured to indicate the elapsed time since the last insulin injection. It will be appreciated that this example and the specific values used in the example are provided for illustrative purposes, and that other configurations of the elapsed timer device and/or other elapsed timer values could be used.

In the example of FIG. 5, the elapsed timer device 500 includes an initialization chamber 505 and four timer elements 591, 592, 593, 594. Each timer element 591, 592, 593, 594 includes a timer chamber 511, 512, 513, 514, with HCM 521, 522, 523, 524, disposed within. Humidity sensor/indicators 531, 532, 533, 534 comprising HICs are sensitive to the RH within timer chambers chamber 511, 512, 513, 514, respectively, and change color when the RH within the timer chambers 511, 512, 513, 514 is below the threshold for the HICs 531, 532, 533, 534. In the example of FIG. 5, the threshold, $Th_1$, for HIC 531 is 30% RH; the threshold, $Th_2$, for HIC 532 is 40% RH; the threshold, $Th_3$, for HIC 533 is 50% RH; and the threshold, $Th_4$, for HIC 534 is 60% RH. It will be appreciated that the threshold values used in this example are provided for illustration purposes and that other threshold values for HICs could be used.

Figure 5A:
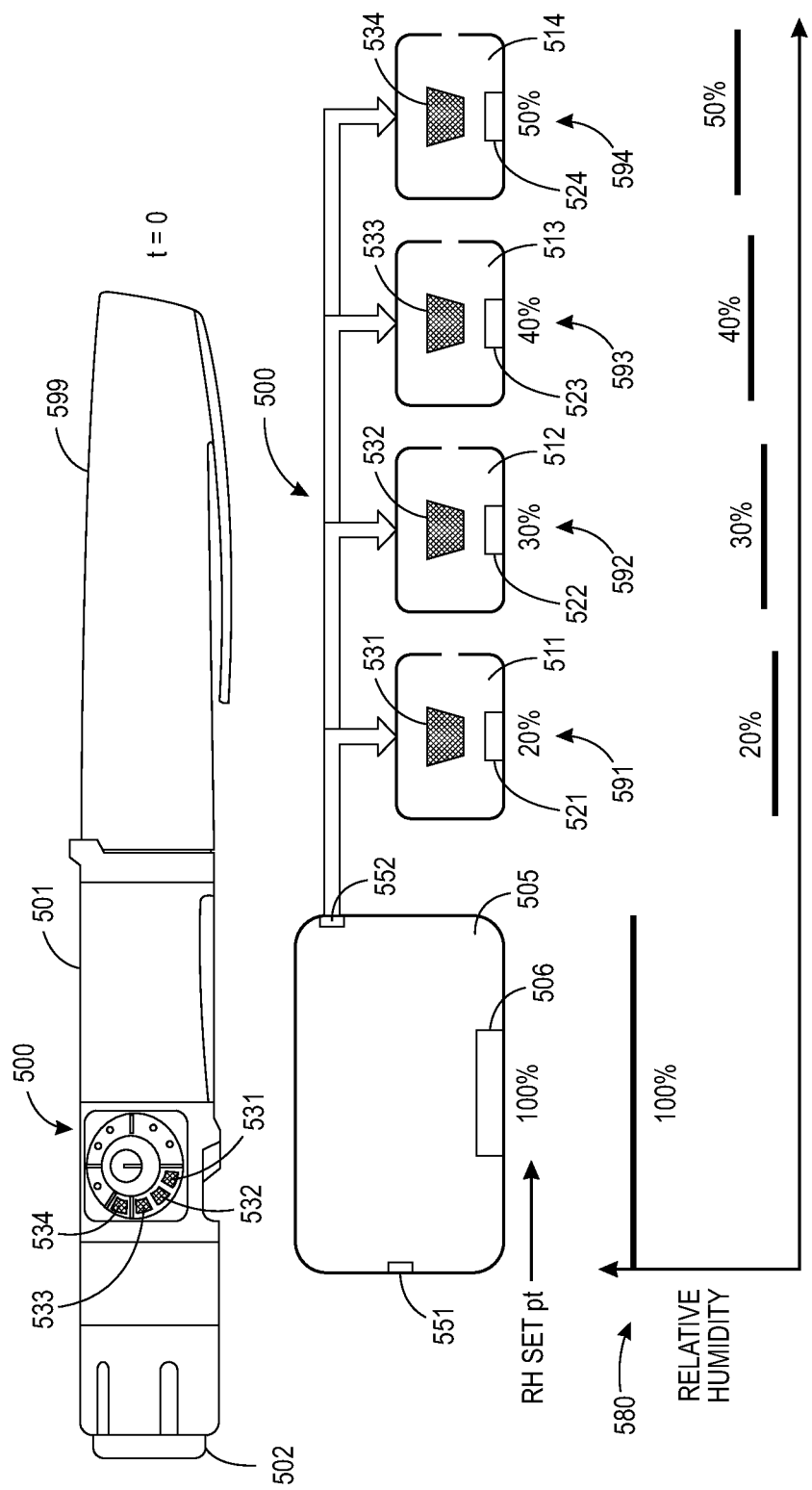
FIGS. 5A through 5G illustrate operation of an elapsed timer device that includes an initialization chamber.

The initialization chamber 505 includes an HCM 506 having adsorption/desorption characteristics that maintain the RH within the initialization chamber 505 at a setpoint humidity, $S_{hci}$, which in this example is 100%. FIG. 5A shows the HICs 531, 532, 533, 534 of the elapsed timer device 500 which are arranged to be viewable on the label 501 of the insulin pen 599. At time $t_0$, prior to initialization of the timer elements, all the HICs 531, 532, 533, 534 are shaded indicating that the RHs in the chambers 511, 512, 513, 514 are below the thresholds $Th_1$, $Th_2$, $Th_3$, $Th_4$, of the HICs 531, 532, 533, 534. The graph 580 in the lower portion of FIG. 5A shows the RH within the initialization chamber 505 and the four timer chambers 511, 512, 513, 514. In this example, the set point, $S_{hci}$, of the HCM 506 of the initialization chamber 505 is 100%; the set point, $S_{hc1}$, of the HCM 521 of the first timer chamber 511 is 20%; the set point, $S_{hc2}$, of the HCM 522 of the second timer chamber 512 is 30%; the set point, $S_{hc3}$, of the HCM 523 of the third timer chamber 513 is 40%; the set point, $S_{hc4}$, of the HCM of the fourth timer chamber 514 is 50%. In FIG. 5A, the RH of each chamber, 505, 511, 512, 513, 514, is at steady state at the setpoints, $S_{hci}$, $S_{hc1}$, $S_{hc2}$, $S_{hc3}$, $S_{hc4}$, of the respective chambers 505, 511, 512, 513, 514, as shown by the graph 580 at the bottom of FIG. 5A. The color of the HICs 531, 532, 533, 534 (shaded in FIG. 5A) indicates that the RH in each timer chamber 511, 512, 513, 514 is below the threshold values, $Th_1$, $Th_2$, $Th_3$, $Th_4$, of the HICs 531, 532, 533, 534.

Figure 5B:
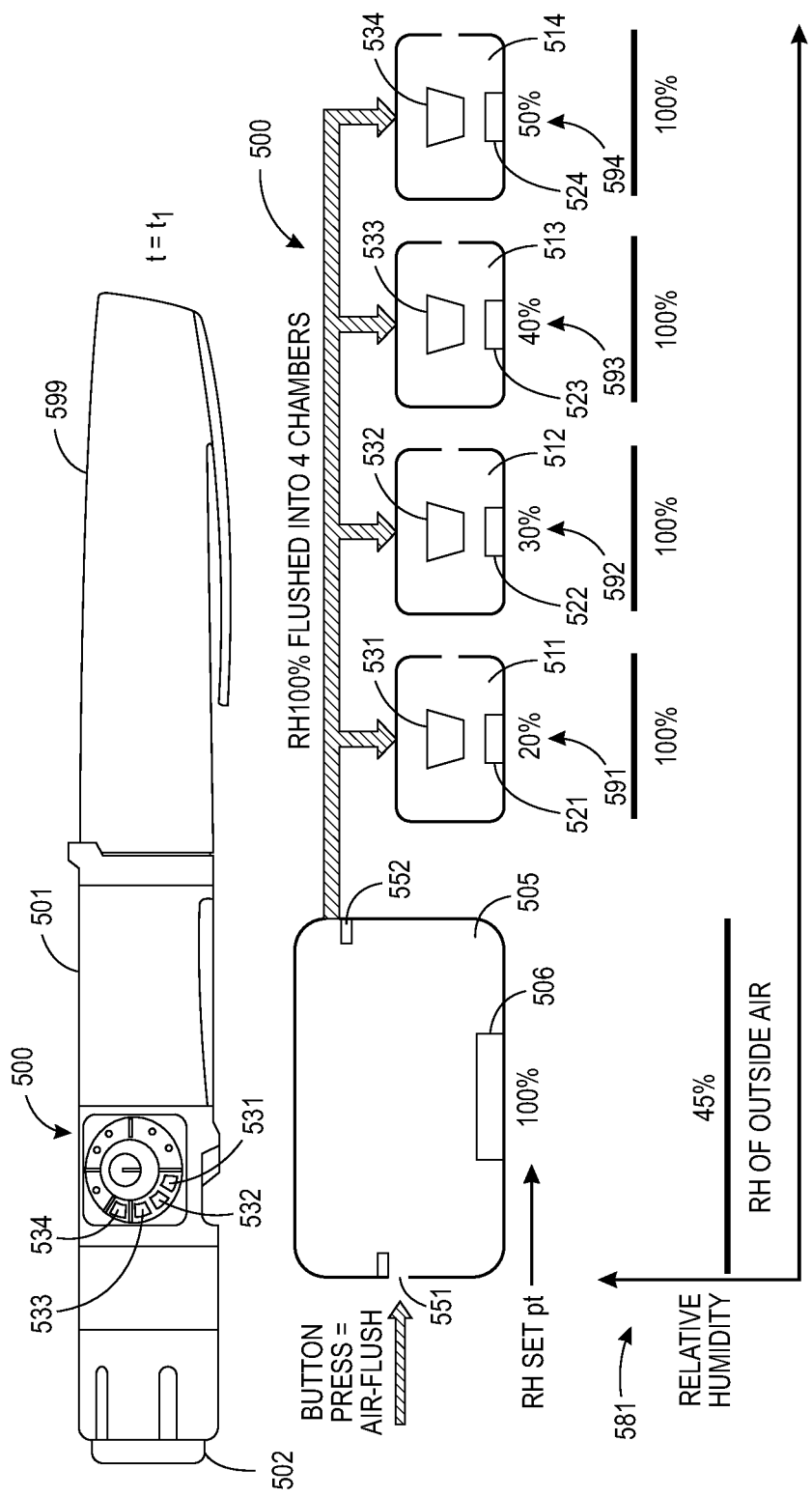

FIG. 5B illustrates the insulin pen 599 having the elapsed timer device 500 incorporated into the label 501 at time $t_1$ just after initialization. The initialization chamber 505 is selectively fluidically coupled to the outside environment through a first initialization structure 551. Each of the timer chambers is selectively fluidically coupled to the initialization chamber 505 through the second initialization structure 552. Initialization of the elapsed timer device 500 involves operating the first and second initialization structures 551 and 552, allowing air from outside the elapsed timer device 500 to enter the initialization chamber and allowing the air from the initialization chamber 505 to enter the timing chambers 511, 512, 513, 514. In some implementations, the one or more of the initialization structures 551, 552 may be small openings, or porous material, such as a gas exchange membrane that allows sufficient air flow through the initialization structure 551, 552 after a threshold pressure is exceeded. In some implementations, one or both of the initialization structures 551, 552 may be valves that can be opened and closed. The initialization structures can be operated when a user pushes a button 502 on the insulin pen 599, which causes a dosage of insulin to be dispensed to the patient and simultaneously operates the initialization structures. For example, in some implementations, the insulin dispensing duration lasts roughly a period of about 1-2 minutes and this period of time is be sufficient to initialize the timer chambers. When the button is released, the initialization structures 551, 552 close and the timer chambers are initialized. Initialization structures 551, 552 block or substantially block air from entering the initialization and/or timer chambers 505, 511, 512, 513, 514 until a subsequent initialization occurs.

During initialization, air from outside the initialization chamber 505, having RH of about 45% in this example, enters the initialization chamber 505 through initialization structure 551. The air from outside the initialization chamber 505 decreases the RH in the initialization chamber 505 to about 45% at time $t_1$ as shown in graph 581. During initialization, the air from the initialization chamber 505 is introduced into each of the timer chambers 511, 512, 513, 514 through the second initialization structure 552, bringing the RH in each timer chamber 511, 512, 513, 514 to about 100% at time $t_1$ as shown in graph 581. The initial color of the HICs 531, 532, 533, 534 (shown as unshaded in FIG. 5B) indicates that the RH in timer chambers 511, 512, 513, 514 is above the threshold values, $Th_1$, $Th_2$, $Th_3$, $Th_4$, of the HICs 531, 532, 533, 534.

The timer chamber 511, HCM 521, and HIC 531 of the first timer element 591 are configured to bring the RH within the first timer chamber 511 from the initialization RH to the RH threshold value, $Th_1$, of the HIC 531 within a first predetermined elapsed time period, $\Delta t_{e1}$, measured from the initialization of the first timer element 591. The timer chamber 512, HCM 522, and HIC 532 of the second timer element 592 are configured to bring the RH within the second timer chamber 512 from the initialization RH to the RH threshold value, $Th_2$, of the HIC 532 within a second predetermined elapsed time period, $\Delta t_{e2}$, measured from initialization of the second timer element 592. The timer chamber 513, HCM 523, and HIC 533 of the third timer element 593 are configured to bring the RH within the third timer chamber 513 from the initialization RH to the RH threshold value, $Th_3$, of the HIC 533 within a third predetermined elapsed time period, $\Delta t_{e3}$, measured from initialization of the third timer element 593. The timer chamber 514, HCM 524, and HIC 534 of the fourth timer element 594 are configured to bring the RH within the third timer chamber 514 from the initialization RH to the RH threshold value, $T_4$, of the HIC 534 within a fourth predetermined elapsed time period, $\Delta t_{e4}$, measured from initialization of the fourth timer element 594. In some implementations, all the timer elements are initialized substantially simultaneously and the first HIC 531 changes color at time $\Delta t_{e1}$ measured from the initialization, the second HIC 532 changes color at $\Delta t_{e2}$, the third HIC 533 changes color at $\Delta t_{e3}$, and the fourth HIC 534 changes color at $\Delta t_{e4}$. In some embodiments, $\Delta t_{e1}$=1 hour, $\Delta t_{e2}$=2 hours, $\Delta t_{e3}$=3 hours, and $\Delta t_{e4}$=4 hours.

Figure 5C:
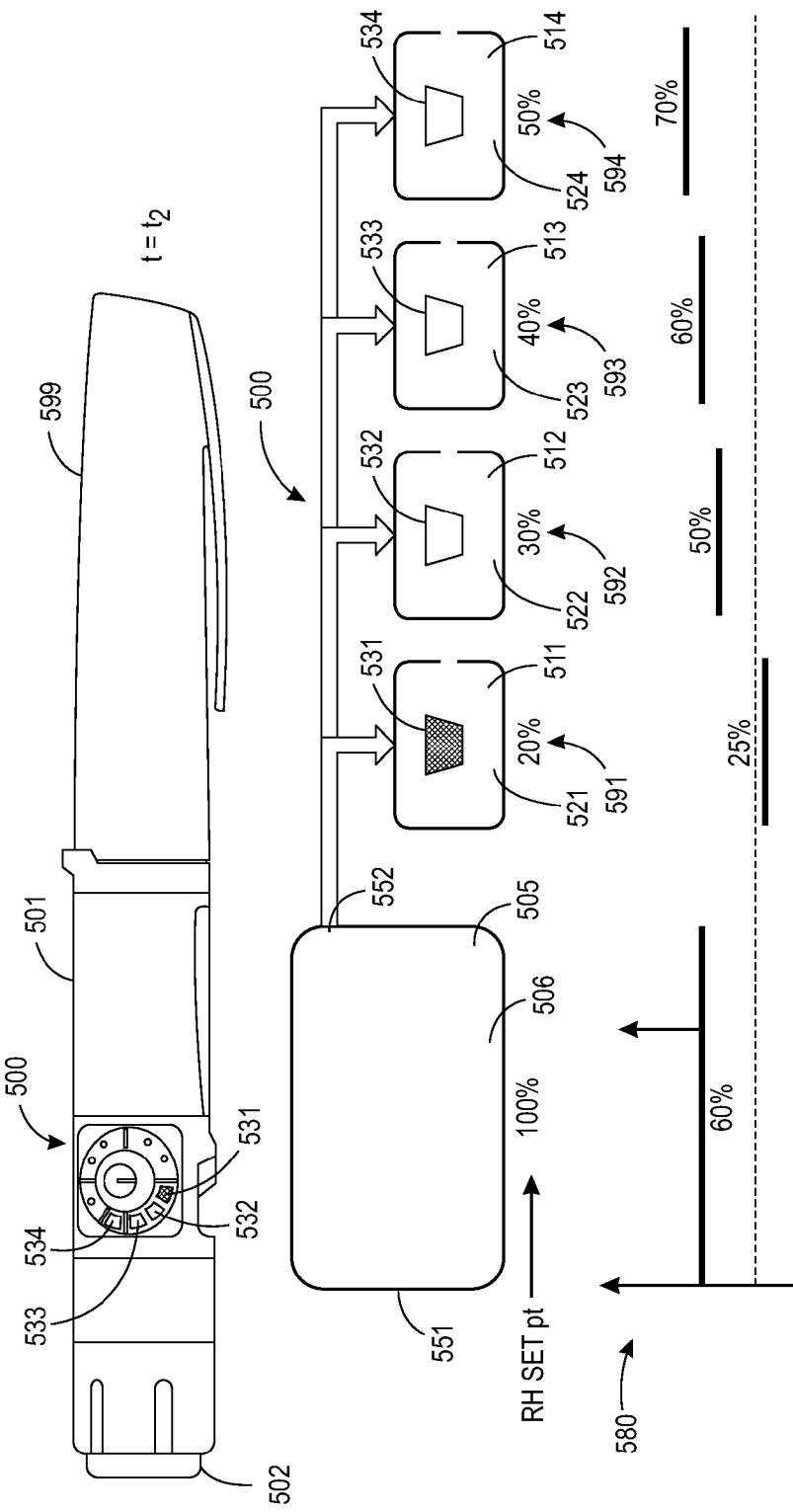

FIG. 5C shows the elapsed timer device 500 incorporated into the label 501 at time $t_2$, after initialization is complete. At time $t_2$, as indicated in graph 582, the RH in the initialization chamber 505 has increased from about 45% to 60%. At time $t_2$, the RH in the first timer chamber 511 has decreased to 25% which is below the threshold, $Th_1$, of the HIC 531. The RH in the second timer chamber 512 has decreased to 50% which is above the threshold, $Th_2$, of the HIC 532; the RH in the third timer chamber 513 has decreased to 60% which is above the threshold, $Th_3$, of the HIC 533; the RH in the fourth timer chamber 514 has decreased to 70% which is above the threshold, $Th_4$, of the HIC 534.

Because the RH (25%) of the first timer chamber 511 is below the threshold, $Th_1$, of the HIC 531 of the first timer chamber 511 ($Th_1$=30% RH in the example of FIG. 5), the HIC 531 has changed color (shown in FIG. 5C as shaded) from the initial color (shown as unshaded in FIG. 5B) indicating that the RH has fallen below the HIC threshold, $Th_1$. The timer chamber 511, HCM 521, and HIC 531 are designed such that the color change of HIC 531 (shown as unshaded to shaded) indicates the passage of the first elapsed time, $\Delta t_{e1}$.

The RHs of the second, third, and fourth timer chambers 512, 513, 514 are above the thresholds of the HICs 532, 533, 534 of the second, third, and fourth timer chambers 512, 513, 514. Thus, the color of the HICs 532, 533, 534 have not changed from the initial color (unshaded) indicating that the RH is above the HIC thresholds, $Th_2$, $Th_3$, $Th_4$, respectively.

Figure 5D:
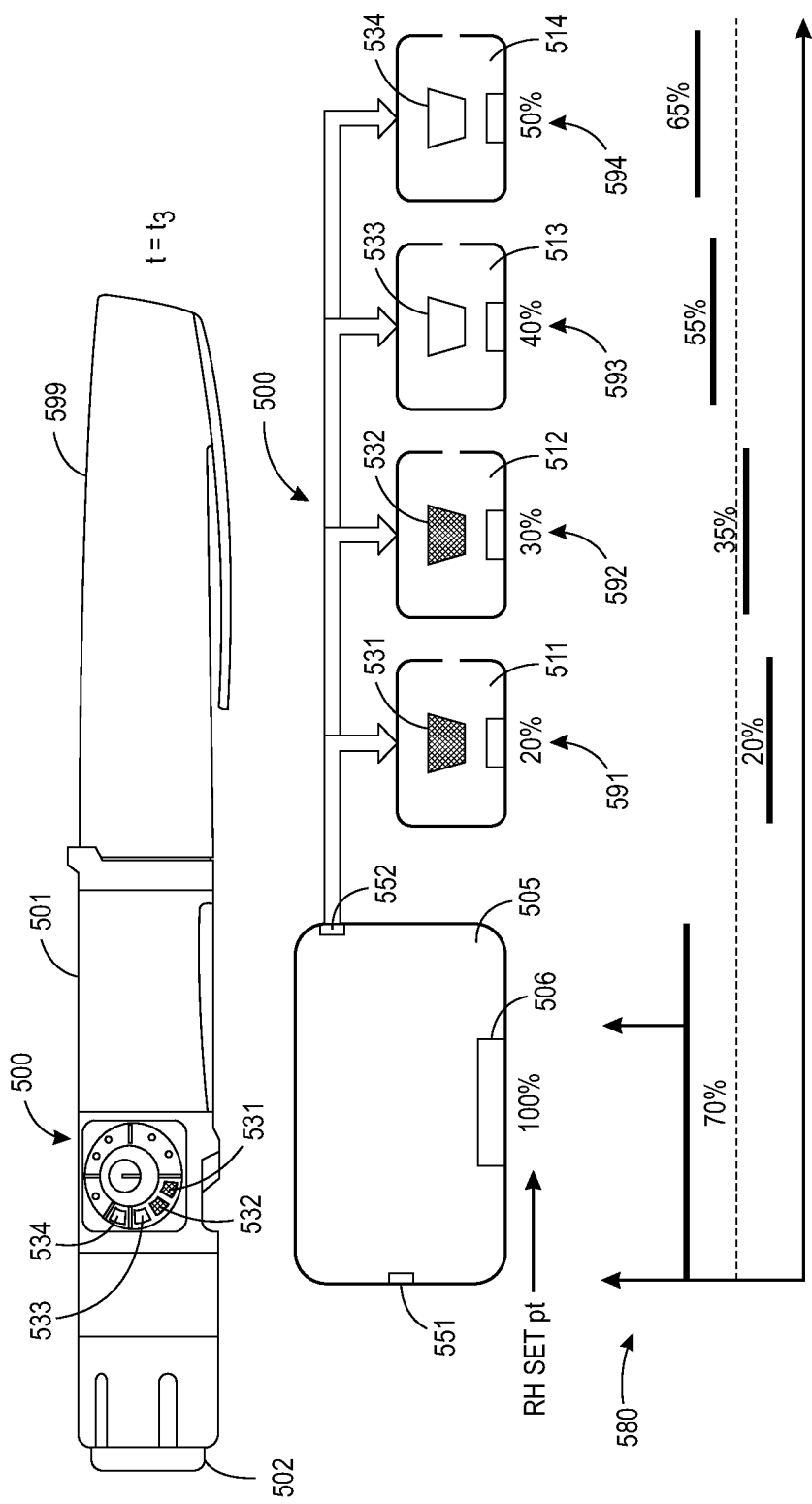

The elapsed timer device 500 is illustrated in FIG. 5D at time $t_3$. At time $t_3$, as indicated in graph 583, the RH in the initialization chamber 505 has increased to 70%. At time $t_3$, the RH in the first timer chamber 511 has decreased to 20% which is the setpoint, $S_{hc1}$, of the HCM 521 and is below the threshold, $Th_1$, of the HIC 531. The RH in the second timer chamber 512 has decreased to 35% which is below the threshold, $Th_2$, of the HIC 532. The RH in the third timer chamber 513 has decreased to 55% which is above the threshold, $Th_3$, of the HIC 533; the RH in the fourth timer chamber 514 has decreased to 65% which is above the threshold, $Th_4$, of the HIC 534.

At time $t_3$, because the RH of the first timer chamber 511 remains below the threshold, $Th_1$, of the HIC 531 of the first timer chamber 511 (30% in the example of FIG. 5), the HIC 531 maintains the color change (shaded) from the initial color (unshaded) indicating that the RH is below the HIC threshold, $Th_1$. Furthermore, because the RH of the second timer chamber 512 has fallen to 35% which is below the threshold, $Th_2$, of the HIC 532 of the second timer chamber 512 ($Th_2$=40% RH in the example of FIG. 5), the HIC 532 has changed color (shaded) from the initial color (unshaded). The timer chamber 512, HCM 522, and HIC 532 are designed so that the color change of the second HIC 532 from unshaded to shaded indicates the passage of the second elapsed time, $\Delta t_{e2}$.

In FIG. 5D, the RHs of the third and fourth timer chambers 513, 514 are above the thresholds of the HICs 533, 534 of the third and fourth timer chambers 513, 514. Thus, the color of the HICs 533, 534 has not changed from the initial color (unshaded).

Figure 5E:
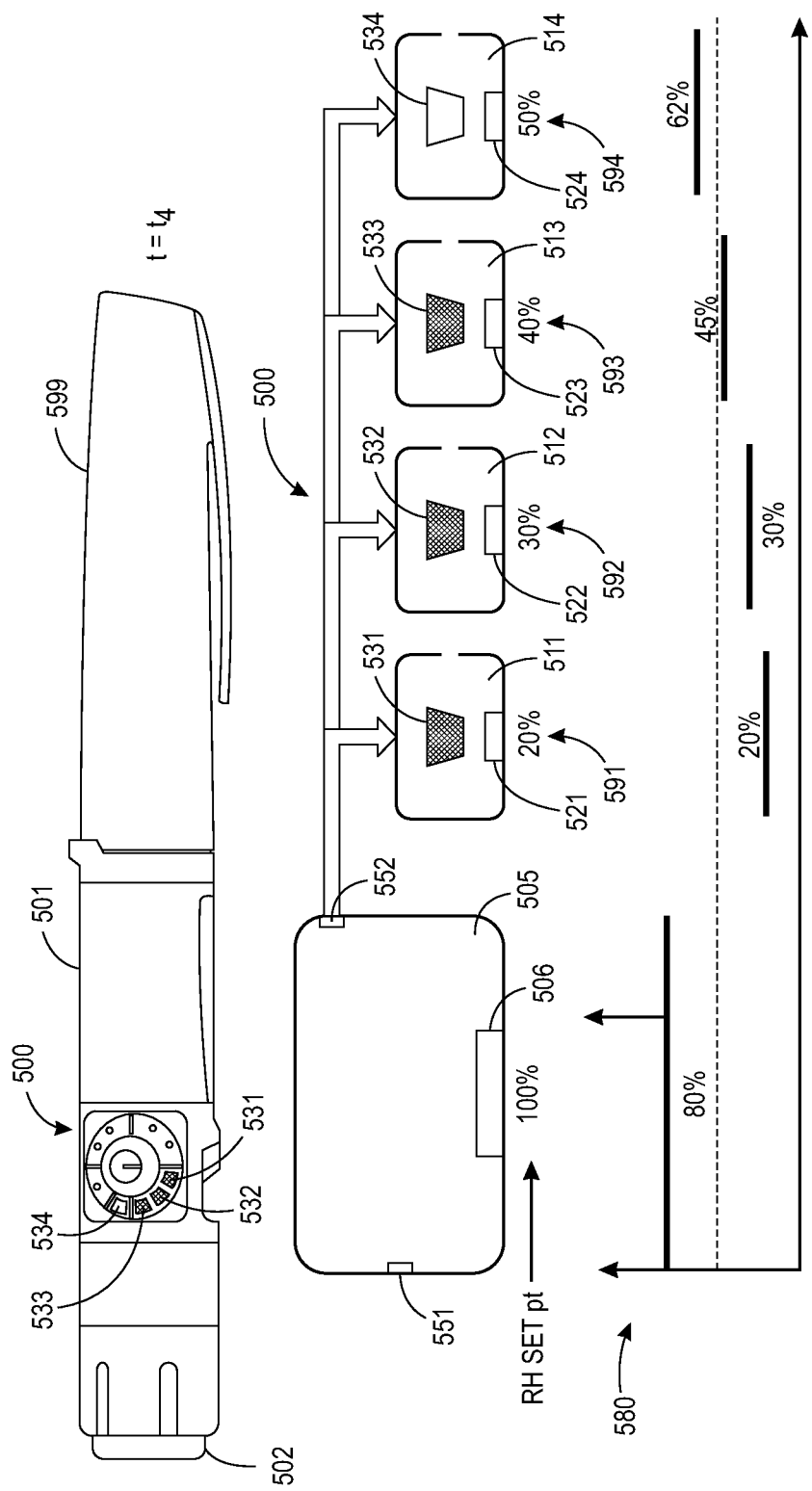

The elapsed timer device 500 is illustrated in FIG. 5E at time $t_4$. At time $t_4$, as indicated in graph 584, the RH in the initialization chamber 505 has increased to 80%. At time $t_4$, the RH in the first timer chamber 511 remains at 20% which is the setpoint, $S_{hc1}$, of the HCM 521 and is below the threshold, $Th_1$, of the HIC 531. The RH in the second timer chamber 512 has decreased to 30% which is the setpoint, $S_{hc2}$, of the HCM 522 and is below the threshold, $Th_2$, of the HIC 532. The RH in the third timer chamber 513 has decreased to 45% which is below the threshold, $Th_3$, of the HIC 533. The RH in the fourth timer chamber 514 has decreased to 62% which is above the threshold, $Th_4$, of the HIC 534.

At time $t_4$, because the RH of the first timer chamber 511 remains below the threshold, $Th_1$, of the HIC 531 of the first timer chamber 511 ($Th_1=30\%$ in the example of FIG. 5), the HIC 531 maintains the color change (shaded) from the initial color (unshaded) indicating that the RH is below the HIC threshold, $Th_1$. Furthermore, because the RH of the second timer chamber 513 remains below the threshold, $Th_2$, of the HIC 532 of the second timer chamber 512, the HIC 532 maintains the color change (shaded) from the initial color (unshaded). Additionally, because the RH of the third timer chamber 513 has fallen to 45% which is below the threshold, $Th_3$, of the HIC 533 of the third timer chamber 513 ($Th_3=50\%$ RH in the example of FIG. 5), the HIC 533 has changed color (shaded) from the initial color (unshaded). The timer chamber 513, HCM 523, and HIC 533 are designed such that the color change from unshaded to shaded of the HIC 533 indicates the passage of the third elapsed time, $\Delta t_{e3}$.

In FIG. 5E, the RH of the fourth timer chamber 514 is above the threshold of the HIC 534 of the fourth timer chamber 514. Thus, the color of the HIC 534 has not changed since from the initial color (unshaded).

Figure 5F:
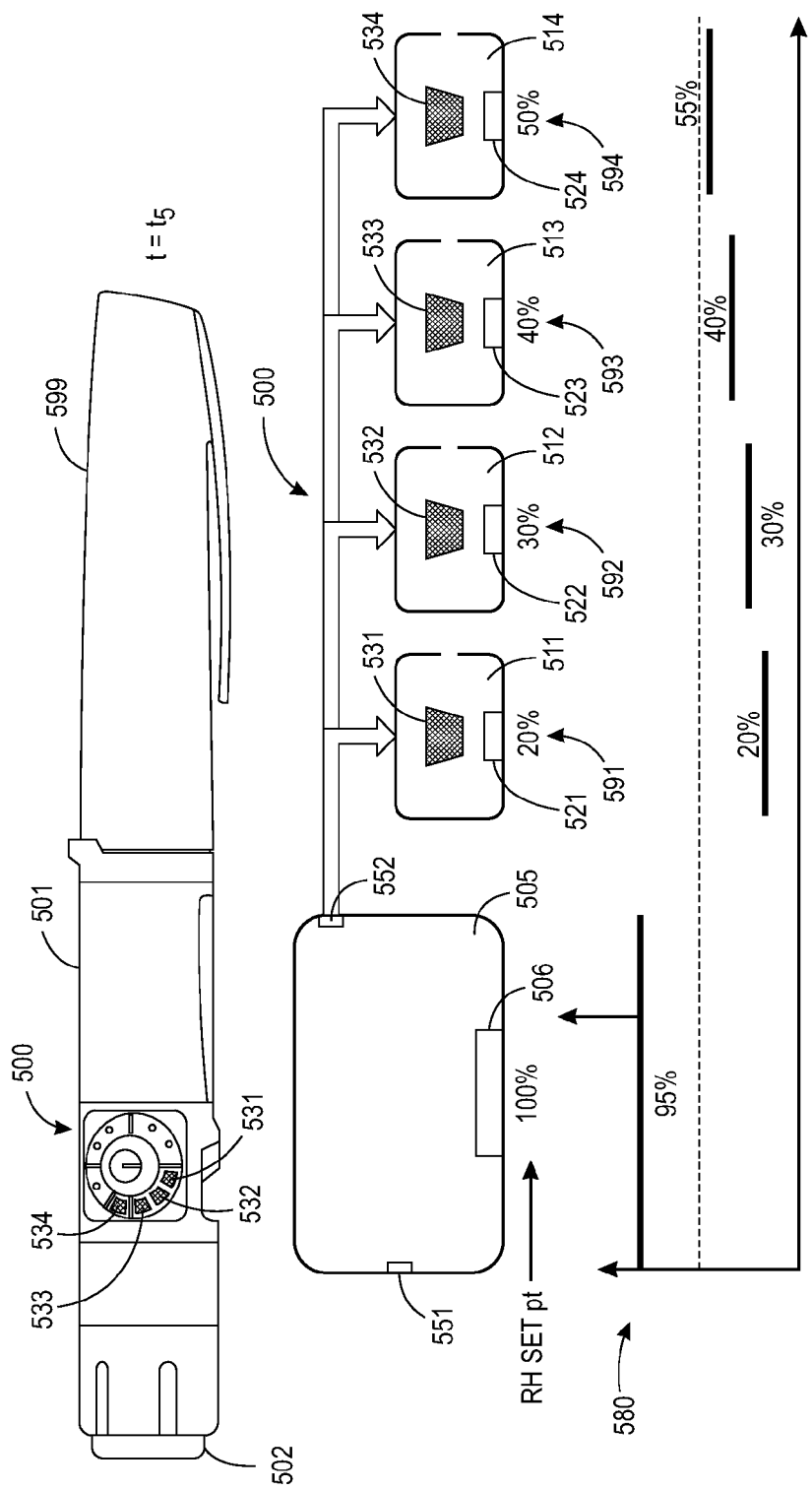

The elapsed timer device 500 is illustrated in FIG. 5F at time $t_5$. At time $t_5$, as indicated in graph 585, the RH in the initialization chamber 505 has increased to 95%. At time $t_5$, the RH in the first timer chamber 511 remains at 20% which is the setpoint, $S_{hc1}$, of the HCM 521 and is below the threshold, $Th_1$, of the HIC 531. The RH in the second timer chamber 512 remains at 30% which is the setpoint, $S_{hc2}$, of the HCM 522 and is below the threshold, $Th_2$, of the HIC 532. The RH in the third timer chamber 513 has decreased to 40% which is the setpoint, $S_{hc3}$, of the HCM 523 and is below the threshold, $Th_3$, of the HIC 533. The RH in the fourth timer chamber 514 has decreased to 55% which is below the threshold, $Th_4$, of the HIC 534.

At time $t_5$, because the RH of the first, second, and third timer chambers 511, 512, 513 remains below the respective thresholds, $Th_1$, $Th_2$, $Th_3$ of the HICs 531, 532, 533, the HICs 531, 532, 533 maintains the color change (shaded) from the initial color (unshaded). Furthermore, because the RH of the fourth timer chamber 514 has fallen to 55% which is below the threshold, $Th_4$, of the HIC 534 of the fourth timer chamber 514 ($Th_4=60\%$ RH in the example of FIG. 5), the HIC 534 has changed color (shaded) from the initial color (unshaded). The timer chamber 514, HCM 524, and HIC 534 are designed such that the color change from unshaded to shaded of the HIC 534 indicates the passage of the fourth elapsed time, $\Delta t_{e4}$.

Figure 5G:
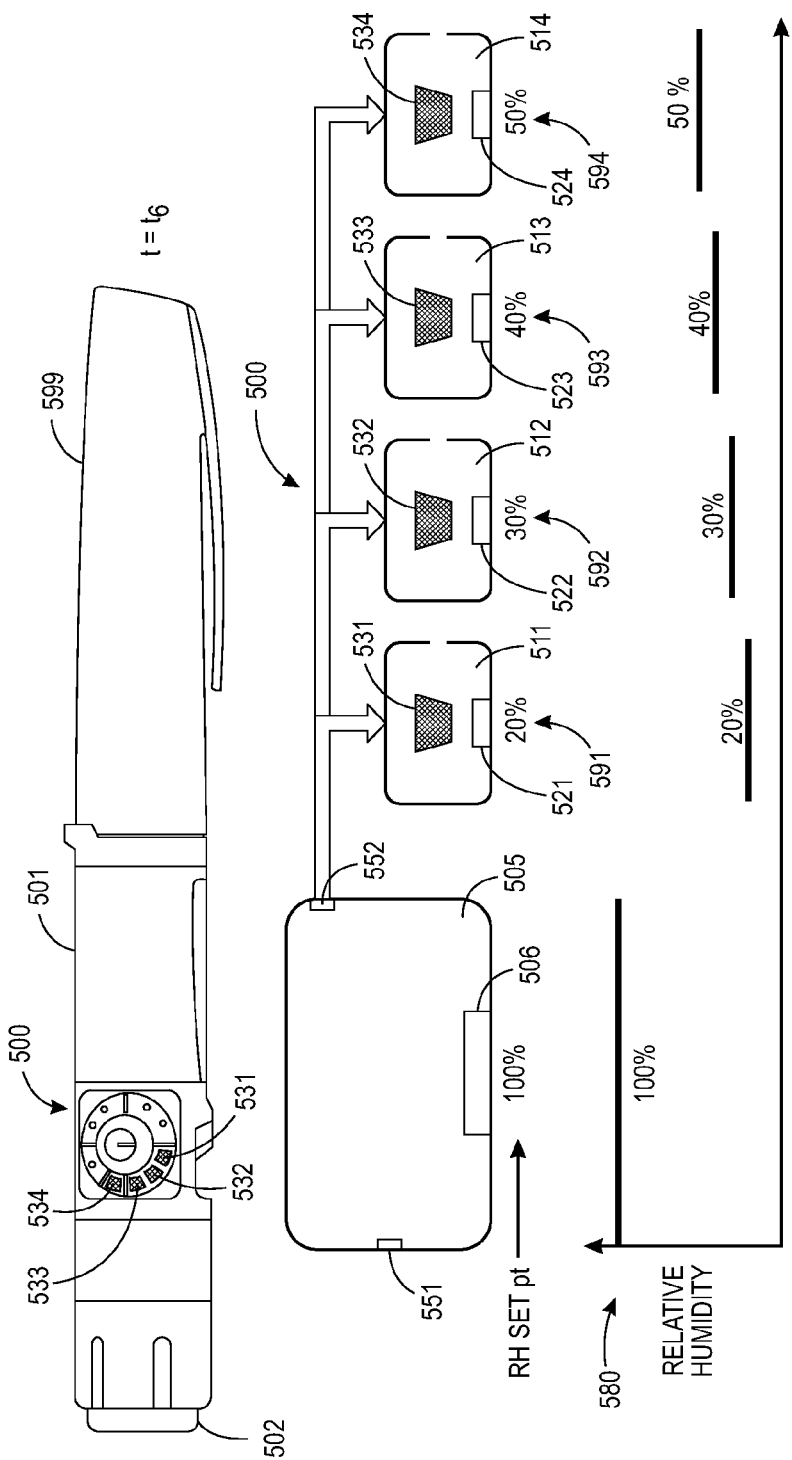

FIG. 5G illustrates the elapsed timer device 500 at time $t_6>t_5$ when the elapsed timer device is again in steady state. The RH in each timing chamber 511, 512, 513 514 is at the setpoint of the HCM 521, 522, 523, 524 for the timer chamber. The RH of the initialization chamber is 100%. At time $t_6$, because the RH of the first, second, third, and fourth timer chambers 511, 512, 513, 514 remains below the respective thresholds, $Th_1$, $Th_2$, $Th_3$, $Th_4$ of the HICs 531, 532, 533, 534 the HICs 531, 532, 533, 534 maintains the color change (shaded) from the initial color (unshaded). In some embodiments, the initialization chamber can be configured to be conditioned, e.g., to 100% RH, within about 1 hour. The timer elements can be reset and restarted as soon as the initialization chamber is conditioned, e.g., less than about 1 hour.

The example of FIG. 5 involves an insulin pen, however, it will be appreciated that the elapsed timer device may indicate the elapsed time with usage of other types of containers including drug containers. For example, in some embodiments, a blister pack comprising a plurality of cells containing a product to be dispensed may include an elapsed timer device configured to indicate an elapsed time from a most recent dispensing of the product from any of the plurality of cells.

Figure 6:
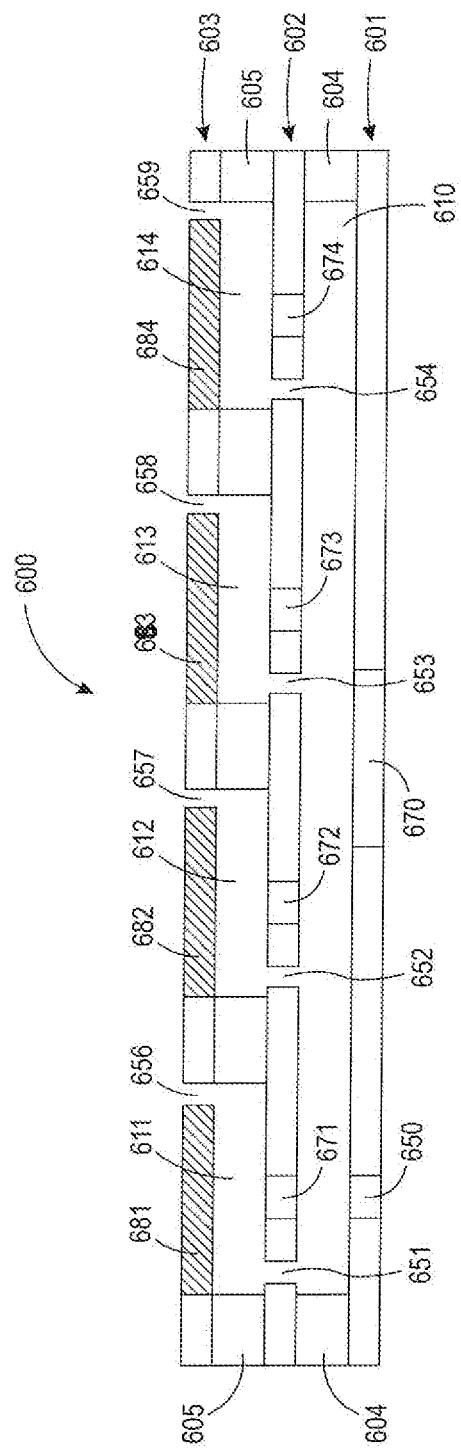
FIG. 6 provides a side cross sectional view of an embodiment of an elapsed timer device having four timer chambers.

A side cross sectional view of an embodiment of an elapsed timer device 600 having four timer chambers 611, 612, 613, 614 and an initialization chamber 610 is illustrated in FIG. 6. The elapsed timer device 600 is formed from layers 601, 602, 603 separated by spacers 604, 605. Spacers 604 separate layers 601 and 602 and spacers 605 separate layers 602 and 603. Initialization structures 650, 651, 652, 653, 654, e.g., small holes, in layers 602 and 603, are arranged to allow air flow during initialization between the outside environment and the initialization chamber 610 (initialization structure 650) and between the initialization chamber 610 and timer chambers 611, 612, 613, 614 (initialization structures 651, 652, 653, 654 respectively). Layer 603 includes small vent holes 656, 657, 658, 659 to facilitate air flow into the timer chambers 611, 612, 613, 614 during initialization. The HCM 670 for the initialization chamber 610 is arranged on and/or embedded at least partially in layer 601. The HCM 671, 672, 673, 674 for each timer chamber 611, 612, 613 614 is arranged on and/or embedded at least partially in layer 602. The humidity sensor/indicators 681, 682, 683, 684 for the timer chambers are arranged on or embedded at least partially within layer 603. The layers 601, 602, 603 and/or spacers 604, 605 may be made of a flexible material, such as poly(ethylene terephthalate) (PET). In some embodiments, at least one of the layers 601, 602, 603 is optically transparent.

Figure 7:
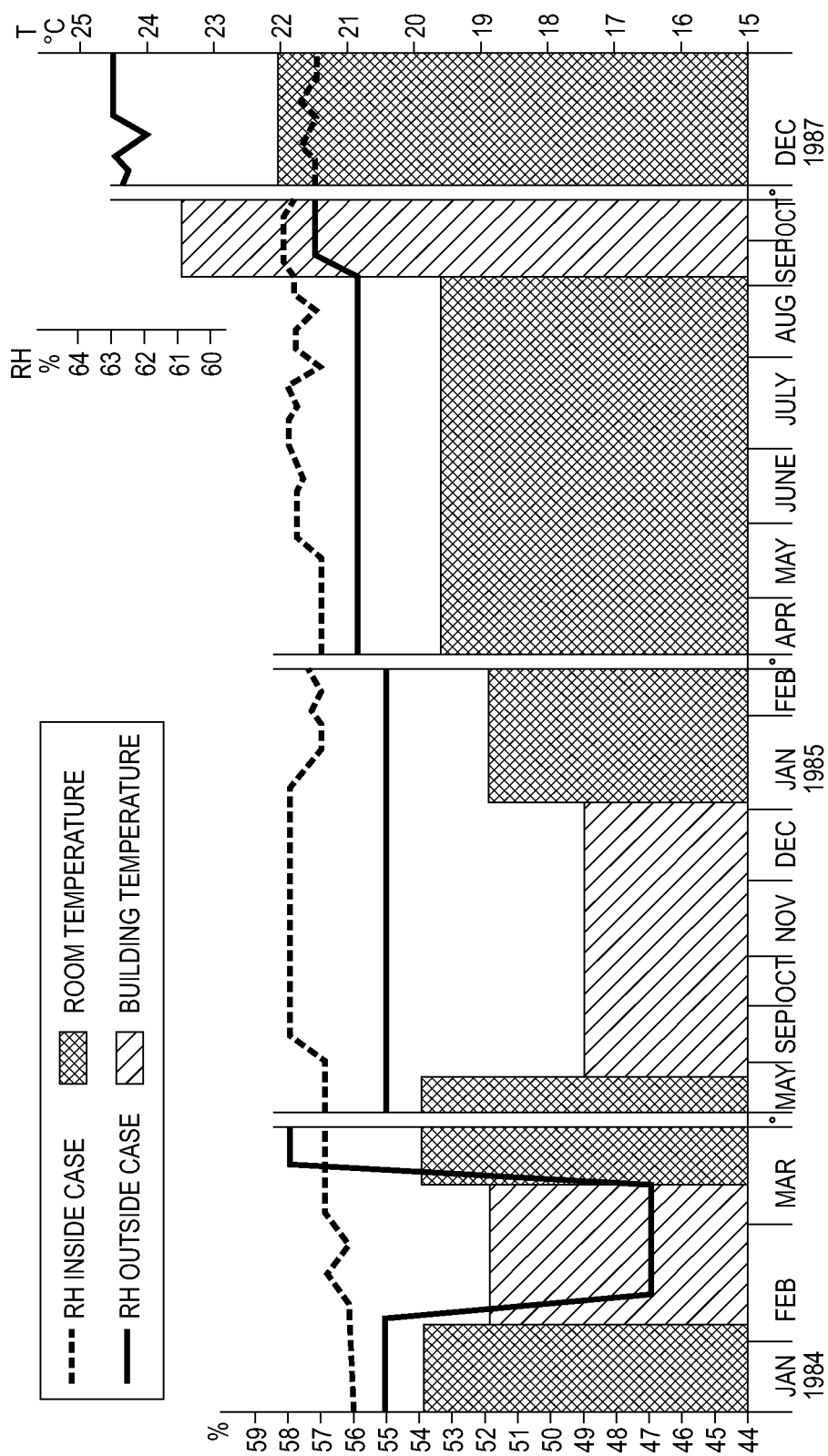
FIG. 7 is a graph indicating the stability of the relative humidity within a chamber having humidity conditioning material disposed therein over a period of about 4 years.

Using HCM and a timer chamber calibrated for a predetermined elapsed time can provide built in temperature compensation (a material property of the HCM) which increases the accuracy of the elapsed timer device. FIG. 7 is a graph indicating the stability of the RH within a chamber having HCM disposed therein over a period of about 4 years provided by Art-Sorb's manufacturer, Fuji Silysia Chemical, Ltd. (http://www.fuji-silysia.co.jp/english/index.html). During this period, although RH outside the chamber and the room temperature and building temperature where the chamber was located fluctuated considerably, the RH within the chamber remained steady at 57%±1%.

Figure 8:
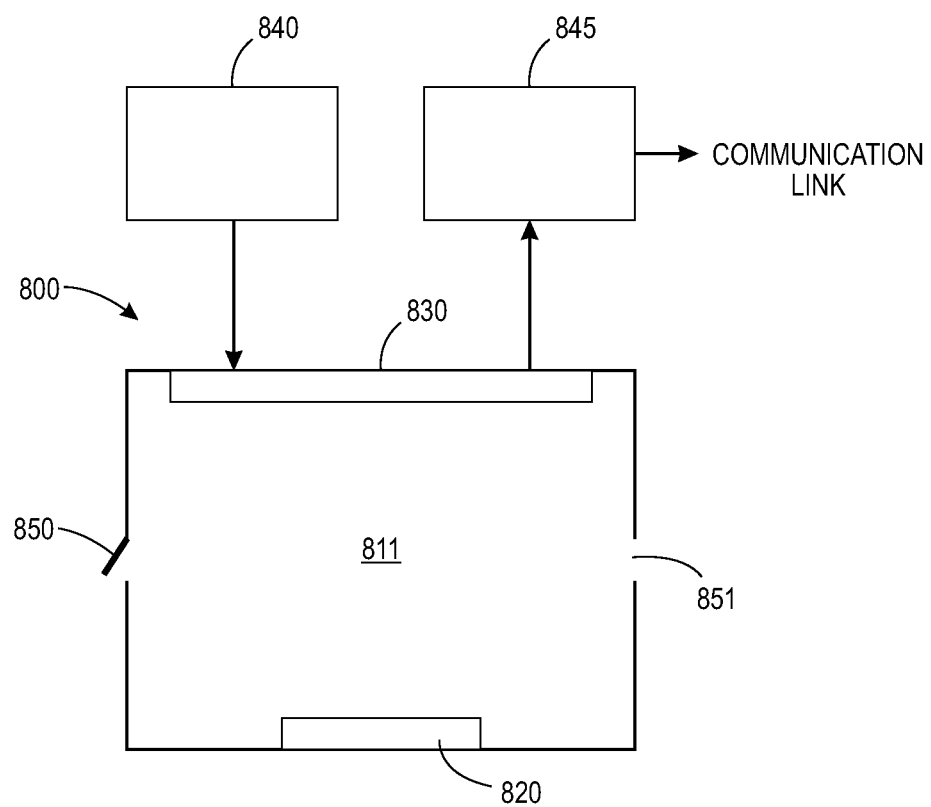
FIG. 8 is a block diagram of an elapsed timer device that includes several optional components, including an optional power supply and optional communication circuitry.

FIG. 8 is a block diagram of an elapsed timer device 800 that includes several optional components, including an optional power supply 840 and optional communication circuitry 845. The humidity sensor/indicator 830 of the elapsed timer device 800 may be a humidity indicator card (HIC) as discussed above in various examples. Elapsed timer devices that use HICs are useful for applications that benefit from a passive device that does not require energy for operation. In some embodiments, the elapsed timer device may rely on technologies that require power, e.g., from a battery, capacitor, or other energy storage device, for operation of various components such as the humidity sensor and/or initialization structure 850. Vent 851 facilitates air exchange between interior and exterior of the timer chamber. Depending on the application, technologies other than the HIC may be used for the humidity sensor/indicator 830, some of which require power for operation. For example, suitable sensors/indicators may include capacitive or resistive humidity sensors. Capacitive and/or resistive humidity sensors can be configured to sense humidity and to generate an electrical signal that indicates the amount of humidity in the chamber. Implementations that include humidity sensors capable of sensing multiple discrete or continuous values in a humidity range may use a single timer element in conjunction with a humidity sensor/indicator that generates a signal that tracks the humidity in the timer chamber as the humidity in the timer chamber rises or falls from the initialization value. The timer chamber 811, HCM 820 disposed within the timer chamber 811, and the humidity sensor/indicator 830 are calibrated so that values of RH within the timer chamber 811 are correlated to elapsed times.

Powered or unpowered versions of the elapsed timer device may include communication circuitry for communicating wirelessly with other devices for remote access of elapsed time. For example, wireless communication for an unpowered implementation of the elapsed timer device may be enabled by radio frequency identification (RFID) technology. In one embodiment, the humidity sensor/indicator may comprise a capacitive or resistive sensor arranged in a resonant circuit wherein a change in the capacitance or resistance of the humidity sensor causes a change in the resonance of the resonant circuit. The change in resonance is detectable by the RFID interrogator. The amount of the change in resonance, which corresponds to the change in capacitance or resistance, corresponds in turn to amount of humidity over a humidity range. The change in humidity can be correlated to an elapsed time.

The approaches disclosed herein provide for a robust elapsed timer that is easy to read (visually or remotely), and is also simple to start and/or to reset. The elapsed timer can be made of inexpensive materials and can be made to be flexible. In some implementations, the elapsed timer can be reusable, e.g., for up to about 100 uses or about 2 weeks. In other implementations the elapsed timer is configured to be a single use device. It can time elapsed time in a range of about 1 hour to about 8 hours with a resolution of less than about +/−20 minutes. The elapsed timer is based on sensing relative humidity, and is not particularly sensitive to temperature variation.

Systems, devices, or methods disclosed herein may include one or more of the features, structures, methods, or combinations thereof described herein. For example, a device or method may be implemented to include one or more of the features and/or processes described herein. It is intended that such device or method need not include all of the features and/or processes described herein, but may be implemented to include selected features and/or processes that provide useful structures and/or functionality.

In the above detailed description, numeric values and ranges are provided for various aspects of the implementations described. These values and ranges are to be treated as examples only, and are not intended to limit the scope of the claims. For example, embodiments described in this disclosure can be practiced throughout the disclosed numerical ranges. In addition, a number of materials are identified as suitable for various implementations. These materials are to be treated as exemplary, and are not intended to limit the scope of the claims.

The foregoing description of various embodiments has been presented for the purposes of illustration and description and not limitation. The embodiments disclosed are not intended to be exhaustive or to limit the possible implementations to the embodiments disclosed. Many modifications and variations are possible in light of the above teaching.

The invention claimed is:

1. An elapsed timer device, comprising:
   at least one timer element, comprising:
      a timer chamber comprising an open volume;
      a timer chamber conditioning material configured and arranged to one or both absorb and desorb a timer chemical from the open volume of the timer chamber to decrease or increase an amount of the timer chemical present within the open volume of the timer chamber toward a threshold level; and
      a sensor spaced apart from the timer chamber conditioning material, the sensor arranged to sense the timer chemical within the open volume of the timer chamber and to indicate elapsed time in response to the threshold level of the timer chemical being present within the open volume of the timer chamber, wherein the timer chamber, timer chamber conditioning material, and the sensor are configured so that the amount of the timer chemical within the open volume of the timer chamber reaches the threshold level within a predetermined time after initialization of the timer element.

2. The device of claim 1, wherein the at least one timer element comprises multiple timer elements.

3. The device of claim 2, wherein:
   each timer chamber of the multiple timer elements is configured to time a different elapsed time; and
   the sensors of the timer elements are configured to sequentially indicate the different elapsed times.

4. The device of claim 1, comprising:
   a first layer having the timer chamber conditioning material arranged on or embedded at least partially within the first layer;
   a second layer that includes the sensor; and
   spacers arranged between the first layer and the second layer, wherein the timer chamber is disposed between the first and second layers.

5. The device of claim 4, further comprising a third layer, wherein an initialization chamber is formed between the third and first layers and the third layer has a timer chamber conditioning material arranged on or embedded at least partially within the third layer.

6. The device of claim 1, wherein the elapsed timer device is flexible.

7. The device of claim 1, wherein the elapsed timer device comprises a flexible polymer.

8. The device of claim 1, further comprising a label, wherein the elapsed timer device forms at least a portion of the label.

9. The device of claim 1, further comprising a product dispenser, and wherein the elapsed timer device is configured to measure elapsed time from a use of the dispenser.

10. The device of claim 9, wherein the product dispenser is configured to dispense a drug.

11. The device of claim 9, wherein the product dispenser is an insulin pen.

12. The device of claim 9, wherein the product dispenser is pill bottle.

13. The device of claim 9, wherein the product dispenser is a blister pack comprising a plurality of cells containing a product to be dispensed, and the elapsed timer device is configured to measure an elapsed time from a dispensing of the product from any of the plurality of cells.

14. An elapsed timer device, comprising:
   at least one timer element, comprising:
      a timer chamber comprising an open volume;
      a humidity conditioning material configured and arranged to one or both absorb and desorb humidity from the timer chamber so as to decrease or increase an amount of humidity present within the open volume of the timer chamber toward a threshold humidity level;

a humidity sensor spaced apart from the humidity conditioning material, the humidity sensor arranged to sense humidity within the open volume of the timer chamber and to indicate elapsed time in response to the threshold humidity level being present within the open volume of the timer chamber, wherein the timer chamber, the humidity conditioning material, and the humidity sensor are configured so that the amount of humidity within the open volume of the timer chamber reaches the threshold humidity level within a predetermined time after initialization of the timer element.

15. The device of claim 14, wherein the timer chamber includes a timer chamber initialization structure, and wherein the initialization of the timer element comprises operation of the timer chamber initialization structure.

16. The device of claim 15, wherein the initialization structure comprises at least one of a hole, a porous material, a gas exchange membrane, and a valve.

17. The device of claim 15, further comprising:
an initialization chamber, wherein the timer chamber initialization structure is arranged so that when the timer chamber initialization structure is open, the timer chamber is fluidically coupled to the initialization chamber; and
a humidity conditioning material disposed within the initialization chamber, wherein at steady-state the humidity conditioning material within the initialization chamber maintains a predetermined humidity within the initialization chamber.

18. The device of claim 17, further comprising:
an initialization chamber initialization structure arranged so that when the initialization chamber initialization structure is open, the initialization chamber is fluidically coupled to an environment external to the elapsed timer device.

19. The device of claim 18, wherein the at least one timer element comprises multiple timer elements.

20. The device of claim 19, wherein, when open, at least one valve fluidically connects the multiple timer chambers to the initialization chamber.

21. The device of claim 19, wherein each timer chamber of the multiple timer elements includes a vent.

22. The device of claim 19, wherein:
timer chambers of the multiple timer elements are configured to time different elapsed times; and
the humidity sensors of the timer elements are configured to sequentially indicate the different elapsed times.

23. The device of claim 14, wherein the humidity sensor comprises a moisture-sensitive chemical that changes color at a predetermined humidity.

24. A method, comprising:
initializing at least one timer element;
decreasing or increasing moisture present within an open volume of the at least one timer chamber toward a threshold humidity level by adsorbing or desorbing moisture from the open volume of a timer chamber of the timer element using a humidity conditioning material;
sensing humidity in the timer chamber using a humidity sensor that is spaced apart from the humidity conditioning material toward the threshold humidity level; and
indicating an elapsed time in response to the threshold humidity level being present within the open volume of the timer chamber, wherein the timer chamber, the humidity conditioning material, and the humidity sensor are configured so that the humidity within the open volume of the timer chamber reaches the threshold humidity level within a predetermined time after initialization of the timer element.

25. The method of claim 24, wherein initializing the timer element comprises opening a timer chamber initialization structure, the opening of the timer chamber initialization structure allowing air having a predetermined humidity from an initialization chamber into the timer chamber.

26. The method of claim 24, wherein;
the at least one timer element comprises multiple timer elements; and
indicating the elapsed time comprises indicating a different elapsed time for each of the multiple timer elements.

27. The method of claim 24, indicating the elapsed time comprises visually indicating the elapsed time.

28. The method of claim 24, further comprising dispensing a product, the dispensing of the product triggering the initializing of the at least one timer element.

29. A method, comprising:
initializing at least one timer element, the initializing starting a chemical reaction that produces a timer chemical;
decreasing or increasing an amount of timer chemical present within an open volume of a timer chamber of the timer element toward a threshold level by adsorbing or desorbing the timer chemical from the timer chamber using a timer chamber conditioning material;
sensing the timer chemical in the timer chamber using a sensor spaced apart from the timer chamber conditioning material; and
indicating an elapsed time in response to the threshold level of the timer chemical being present within the open volume of the timer chamber, wherein the timer chamber, the timer chamber conditioning material, and the sensor are configured so that the amount of the timer chemical within the open volume of the timer chamber reaches the threshold level within a predetermined time after initialization of the timer element.

* * * * *